United States Patent
Ezure et al.

(10) Patent No.: US 7,745,171 B2
(45) Date of Patent: Jun. 29, 2010

(54) CELL-FREE PROTEIN SYNTHESIS METHOD USING INSECT CELL EXTRACT SOLUTION

(75) Inventors: Toru Ezure, Osaka (JP); Shoken Higashide, Osaka (JP); Takashi Suzuki, Osaka (JP); Masaaki Ito, Osaka (JP); Koki Endo, Osaka (JP)

(73) Assignee: Shimadzu Corporation, Kyoto (JP)

( * ) Notice: Subject to any disclaimer, the term of this patent is extended or adjusted under 35 U.S.C. 154(b) by 327 days.

(21) Appl. No.: 11/987,981

(22) Filed: Dec. 6, 2007

(65) Prior Publication Data

US 2008/0221311 A1 Sep. 11, 2008

Related U.S. Application Data

(62) Division of application No. 10/742,766, filed on Dec. 23, 2003, now Pat. No. 7,323,332.

(30) Foreign Application Priority Data

Dec. 27, 2002 (JP) ............................. 2002-382415

(51) Int. Cl.
*C12P 21/06* (2006.01)
*C07K 1/00* (2006.01)
(52) U.S. Cl. ..................... 435/68.1; 435/348
(58) Field of Classification Search .................. None
See application file for complete search history.

(56) References Cited

U.S. PATENT DOCUMENTS

| | | | |
|---|---|---|---|
| 5,866,317 A | 2/1999 | Miyazawa | |
| 6,103,489 A * | 8/2000 | Arakaki et al. | 435/68.1 |
| 7,312,060 B2 * | 12/2007 | Rothschild et al. | 435/194 |
| 7,323,332 B2 * | 1/2008 | Ezure et al. | 435/358 |
| 2002/0034814 A1 * | 3/2002 | Atabekov et al. | 435/235.1 |
| 2005/0255542 A1 * | 11/2005 | Shirouzu et al. | 435/68.1 |

FOREIGN PATENT DOCUMENTS

| | | |
|---|---|---|
| CN | 1 088584 | 6/1994 |
| JP | 2000-224990 | 8/2000 |
| JP | 2000-325076 | 11/2000 |
| WO | 98/48617 | 11/1998 |

OTHER PUBLICATIONS

Japanese Office Action dated May 13, 2008 issued for JP 2003-351377, which is based on JP 2002-382415, which is a base application of the above-identified U.S. application.

Addison, Randolph, "A Cell-Free Translation-Translocation System Reconstituted with Subcellular Fractions from the Wall-less Variant *fz;sg;os-1V* of *Neurospora crassa*," Fungal Genet. and Biol., 1998, vol. 24(3), pp. 345-353.

Arakawa, T. et al., "Freeze-thawing method: a bleeding method from lepidopteran larvae utilizing a spontaneous insect body contraction after a freezing-thawing treatment," J. Appl. Ent., 1999, vol. 123(7), pp. 443-446.

Tarui, H., et al., "A Novel Cell-Free Translation/Glycosylation System Prepared from Insect Cells," Journal of Bioscience and Bioengineering, vol. 90, No. 5, pp. 508-514, 2000.

Tarui, H., et al., "Establishment and Characterization of Cell-Free Translation/Glycosylation in Insect Cell (*Spodoptera frugiperda* 21) Extract Prepared with High Pressure Treatment," Appl. Microbiol. Biotechnol., vol. 55, pp. 446-453, 2001.

Swerdel M R et al: "Cell-Free Translation in Lysates From *Spodoptera-frugiperda* Lepidoptera Noctuidae Cells" Comparative Biochemistry and Physiology B, vol. 93, No. 4, 1989, pp. 803-806, XP002272558. ISSN:0305-0491.

Maruniak J E et al: "Susceptibility of Insect Cells and Ribosomes to Richin" Comparative Biochemistry and Physiology B, vol. 96, No. 3, 1990, pp. 543-548, XP002272559. ISSN: 0305-0491.

Doverskog M et al: "Determination of NADH-dependent glutamate synthase (Gogat) in *Spodoptera frugiperda* (sf9) insect cells by a selective H/N NMR in vitro assay" Journal of Biotechnology, Elsevier Science Publishers, Amsterdam, NL, vol. 79, No. 1, Apr. 14, 2000, pp. 87-97, XP004222568. ISSN: 0168-1656.

Sambrook, J, Russel, D.: "Molecular Cloning, Third Edition" 2001, Cold Spring Harbour, New York, XP002272561. 9.87, 9.88, 17.36, 17.37.

Eva Lindskog (2006), Physiology and Productivity of Serum-Free *Spodoptera frugiperda* Sf9 Insect Cell Cultures. School of Biotechnology, Department of Bioprocess Technology, Royal Institute of Technology, SE-106 91, Stockholm, Sweden, Page Nos. 1, 7 and 8.

* cited by examiner

*Primary Examiner*—Herbert J. Lilling
(74) *Attorney, Agent, or Firm*—Wenderoth, Lind & Ponack, L.L.P.

(57) ABSTRACT

The present invention provides a preparation method of an insect cell extract solution for cell-free protein synthesis, the insect cell extract solution, a protein synthesis method in a cell-free system, which uses the insect cell extract solution, and a kit for cell-free protein synthesis containing the insect cell extract solution. The extract solution is easily prepared by the method of the present invention and can synthesize a higher amount of protein than by extract solutions prepared by conventional methods.

10 Claims, 5 Drawing Sheets

CELL-FREE PROTEIN SYNTHESIS METHOD USING INSECT CELL EXTRACT SOLUTION

This is a divisional of Ser. No. 10/742,766, filed Dec. 23, 2003, which is herein incorporated by reference in its entirety.

TECHNICAL FIELD OF THE INVENTION

The present invention relates to a method for preparing an insect cell extract solution usable for cell-free protein synthesis, said insect cell extract solution, a cell-free synthesis method of a protein using said insect cell extract solution, and a kit for cell-free protein synthesis, containing said insect cell extract solution.

BACKGROUND OF THE INVENTION

In recent years, genetic information of many organisms, such as human genome, has been decoded. Under the circumstances, functional analysis of proteins and creation of genomic medicine based on such genetic information have been attracting attention for postgenomic studies. Application and utilization of proteins corresponding to such genetic information for pharmaceutical products and the like requires easy synthesis of extensive kinds of proteins in a short time.

At present, expression systems using viable cells (hereinafter sometimes to be referred to as "cell-system") of yeast, insect cell and the like by the gene recombination technique have been widely utilized as the production methods of proteins. However, viable cells show a propensity toward elimination of exogenous proteins for their functional retention, and there are many proteins that cannot be expressed easily since expression of cytotoxic proteins in viable cells prevents cell growth.

On the other hand, as a production method of protein free of a cell-system, cell-free protein synthesis has been known, which includes adding a substrate, an enzyme and the like to a cell rupture, extract solution and the like to provide a wide choice of genetic information translation systems of organisms in test tubes, and reconstructing a synthetic system capable of linking the necessary number of amino acid residues in a desired order using an mRNA encoding an object protein. Such a cell-free protein synthesis is relatively free of the limitation imposed on the above-mentioned cell-system protein synthesis, and is capable of synthesizing proteins without killing the organism. In addition, because the production of protein does not accompany operations of culture and the like, the protein can be synthesized in a short time as compared to cell-systems. Moreover, inasmuch as the cell-free protein synthesis also affords a large scale production of proteins consisting of amino acid sequences not utilized by the organism, it is expected to be a promising expression method. As a cell rupture or extract solution to be applied to the cell-free protein synthesis, use of various substances of biological derivation has been considered and investigations are underway. Of such substances, since insect cells do not require, unlike many mammalian culture cells, culture under a carbon dioxide atmosphere, can be cultured in a serum-free medium, and can express in a large amount in a cell-system while retaining the inherent biological activity with posttranslational modification, they are used for the expression of various proteins. If the insect cell can be used for a cell-free system, posttranslational modification, such as glycosylation and the like, is fully expected to be applicable. Thus, the development of utilization of the insect cell is drawing attention.

Conventionally, for extraction from an insect cell for the preparation of an extract solution for cell-free protein synthesis, a method comprising reducing the pressure applied to an insect cell after pressurization in an inert gas atmosphere, thereby to rupture the insect cell to allow for extraction, is known (e.g., JP-A-2000-325076). This method nevertheless requires special devices and tools for extraction from the insect cell, and the operation is complicated. Moreover, complicated manipulations are necessary for the setting of the conditions, because protein synthesis ability of the cell-free system vastly change depending on the number of cells, nitrogen gas pressure and pressurization time during the preparation of the extract solution. In addition, the amount of protein synthesized using the extract solution obtained by this method is extremely small, which is of the level that can be measured by the uptake of the radiolabeled amino acid.

Therefore, the development of an insect cell-derived extract solution, which is easy to prepare and which affords synthesis of a large amount of protein, and the preparation method thereof is desired.

SUMMARY OF THE INVENTION

The present invention has been made to solve the above-mentioned problems and aims at providing a preparation method of an insect cell extract solution for cell-free protein synthesis, which solution is easy to prepare and affords synthesis of a protein in a higher amount than by conventional solutions, the insect cell extract solution, a cell-free protein synthesis method using the insect cell extract solution, and a kit for cell-free protein synthesis, which contains the insect cell extract solution.

As a result of the intensive studies conducted by the present inventors in an attempt to solve the above-mentioned problems, the present invention has been completed. Accordingly, the present invention provides the following.

(1) A method for preparing an insect cell extract solution for cell-free protein synthesis, which comprises at least a step of rapidly freezing an insect cell suspended in a solution for extraction, to allow for extraction from the insect cell.

(2) The method of the above-mentioned (1), wherein the extraction from the insect cell comprises thawing the above-mentioned insect cell after rapid freezing and subjecting the cell to centrifugation.

(3) The method of the above-mentioned (1) or (2), wherein the insect cell is frozen with liquid nitrogen.

(4) The method of the above-mentioned (2) or (3), wherein the insect cell is thawed in a water bath or ice-water bath at −10° C.-20° C.

(5) The method of any of the above-mentioned (1) to (4), wherein the solution for extraction comprises a protease inhibitor.

(6) The method of any of the above-mentioned (1) to (5), further comprising a nuclease treatment.

(7) The method of any of the above-mentioned (1) to (6), wherein the insect cell is a culture cell derived from *Trichoplusia ni* ovum or *Spodoptera frugiperda* ovary cell, or a combination of a cell derived from *Trichoplusia ni* ovum and a cell derived from *Spodoptera frugiperda* ovary cell.

(8) An insect cell extract solution for cell-free protein synthesis, which is prepared by a method of any of the above-mentioned (1) to (7).

(9) A method for cell-free protein synthesis, which comprises use of the insect cell extract solution of the above-mentioned (8).

(10) The method of the above-mentioned (9), which comprises use of an exogenous mRNA having a cap structure.

(11) A kit for cell-free protein synthesis, which comprises the insect cell extract solution of the above-mentioned (8).

DETAILED DESCRIPTION OF THE INVENTION

Figure 1:
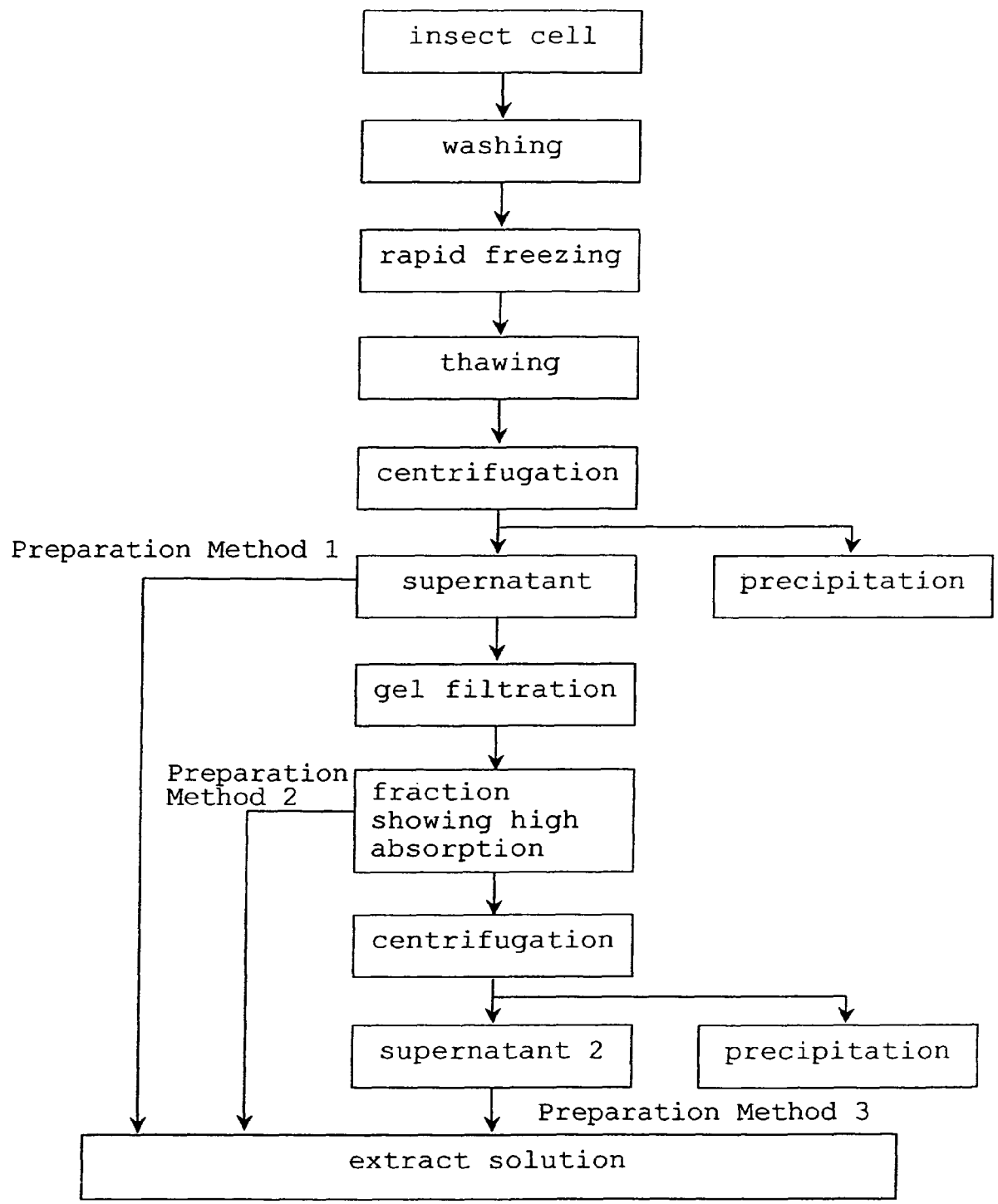
FIG. 1 is a simplified flow chart showing preferable Preparation Methods 1-3 of the present invention.

The "cell-free protein synthesis" in the present specification means a protein synthesis using a cell-free translation system to synthesize a protein by reading the information of exogenous mRNA. As used herein, the "protein" synthesized in the cell-free system according to the synthesis method of the present invention encompasses any peptide having any molecular weight, which consists of plural amino acid residues, i.e., from low molecular weight peptides to high molecular weigh peptides. The "protein" in the present specification includes glycosylated glycoproteins.

Embodiment of the Invention

The present invention is explained in detail in the following.

The present invention provides a method for preparing an insect cell extract solution for cell-free protein synthesis, which characteristically comprises at least a step of rapidly freezing an insect cell suspended in a solution for extraction, thereby to allow for extraction from the insect cell. By preparing such an insect cell extract solution, the cells can be ruptured under milder conditions as compared to the above-mentioned conventional method described in JP-A-2000-325076, and the components essential for cell-free protein synthesis can be taken out from the cell without damage, which in turn affords easy preparation of an extract solution having higher capacity to synthesize a protein in a cell-free system than an extract solution produced by a conventional method. According to the method of the present invention, moreover, contamination with RNase and the like from the tools and the like can be prevented, and incorporation of a substance inhibiting translation reaction, which is of concern in the case of cell rupture methods using a reagent such as detergent and the like, can be avoided.

The preparation method of the present invention requires rapid freezing of insect cells suspended in a solution for extraction. In the preparation method of the present invention, by the "rapid freezing" is meant that an insect cell is frozen in not longer than 10 sec, preferably not longer than 2 sec, after subjecting the cell to a freezing treatment. When the insect cell is not rapidly frozen in the present invention, the components essential for protein synthesis may be inactivated, and the above-mentioned effect of the present invention may not be achieved.

As mentioned above, the insect cell is rapidly frozen at a temperature of generally not higher than −80° C., preferably not higher than −150° C. This is because the protein synthesis ability tends to be degraded when the cell is rapidly frozen at a temperature exceeding −80° C., since the components essential for the protein synthesis are inactivated.

The above-mentioned rapid freezing of the insect cell can be realized by, for example, using an inert gas such as liquid nitrogen, liquid helium and the like, and the like. It is preferable to use liquid nitrogen because it is easily available and economical.

According to the preparation method of the present invention, as long as at least a step for rapidly freezing an insect cell suspended in a solution for extraction is included in the extraction from an insect cell, other steps are free of any particular limitation. For example, insect cells may be ruptured and extracted by various methods conventionally employed for obtaining an extract solution for cell-free protein synthesis from *Escherichia coli*, wheat germ and the like, such as a method comprising mashing the cells in a mortar with a pestle, a method using a dounce homogenizer, a method using glass beads and the like. Because insect cells are easily ruptured as compared to an extract solution for cell-free protein synthesis obtained from *Escherichia coli*, wheat germ and the like, and because an extract solution having high protein synthesis ability can be obtained since the rupture method including freeze-thawing alone affords an extract solution containing the components essential for protein synthesis in a state of retaining the activity, it is preferable to rupture the above-mentioned insect cell by rapidly freezing, thawing and centrifuging the insect cell.

When the above-mentioned rapidly frozen insect cell is to be thawed and centrifuged, the cell is thawed in a water bath or ice-water bath at −10° C. to 20° C., by leaving the cell to stand at room temperature (25° C.) and the like. To prevent inactivation of the components essential for protein synthesis and to certainly prevent degradation of protein synthesis ability, the cell is preferably thawed in a water bath or ice-water bath at 0° C. to 20° C. (particularly 4° C. to 10° C.). The thawed insect cell is centrifuged under the conditions generally employed in the pertinent field (10,000×g-50,000×g, 0° C.-10° C., 10 min-60 min). The supernatant after centrifugation contains an extract of the object insect cell.

The insect cell to be used in the present invention is not subject to any particular limitation, and, for example, cells derived from insects of *Lepidoptera, Orthoptera, Diptera, Hymenoptera, Coleoptera, Coleoptera, Neuroptera, Hemiptera* and the like can be used. Of these, cells derived from insects of *Lepidoptera, Hemiptera* and the like are preferable, because many culture cell lines thereof have been established. Furthermore, the insect cell in the present invention may be a cell derived from any tissue, and, for example, blood cell, gonad-derived cell, fat body-derived cell, embryo-derived cell, hatch larva-derived cell and the like can be used without any particular limitation. Of these, gonad-derived cell, which is considered to have high protein production capability, is preferably used. Particularly, use of High Five (manufactured by Invitrogen), which is a cell derived from the ovum of *Trichoplusia ni* or Sf21 (manufactured by Invitrogen), which is a cell derived from *Spodoptera frugiperda* ovary cell, as an insect cell is preferable, because they have high protein synthesis ability in a cell-system and can be cultured in a serum-free medium.

In the present invention, the cell is not limited to an insect cell derived from a single tissue of a single species of insect, and it may be derived from plural kinds of tissues of a single species of insect, or a single kind of tissue of plural species of insects, or derived from plural kinds of tissues of plural species of insects.

A solution for extraction to be used for the preparation method of the present invention is not particularly limited, but it preferably contains at least a protease inhibitor. When a solution for extraction containing a protease inhibitor is used, the protease activity contained in an extract derived from the insect cell is inhibited, thereby preventing undesired decomposition of the active protein in the extract due to protease, which in turn effectively draws out advantageously the protein synthesis ability that the extract derived from the insect cell has.

The above-mentioned protease inhibitor is not particularly limited as long as it can inhibit the activity of protease, and, for example, phenylmethanesulfonyl fluoride (hereinafter sometimes to be referred to as "PMSF"), aprotinin, bestatin, leupeptin, pepstatin A, E-64 (L-trans-epoxysuccinyl-L-leucylamido(4-guanidino)butane), ethylenediaminetetraacetic acid, phosphoramidon and the like can be used. Since an extract solution derived from an insect cell contains serine protease, the use of PMSF, which works as an inhibitor having high specificity to serine protease, is preferable among those mentioned above. It is possible to use not only one kind of protease inhibitor but also a mixture (protease inhibitor cocktail) of several kinds of protease inhibitors.

The content of the protease inhibitor in the solution for extraction is free of any particular limitation, but it is preferably 1 μM-50 mM, more preferably 0.01 mM-5 mM, because decomposition of the enzyme necessary for the action of the present invention can be preferably inhibited. This is because the decomposition activity of protease often cannot be suppressed sufficiently when the protease inhibitor content is less than 1 μM, and the protein synthesis reaction tends to be inhibited when the protease inhibitor content exceeds 50 mM.

The solution for extraction to be used for the present invention preferably contains, in addition to the above-mentioned protease inhibitor, at least a potassium salt, a magnesium salt, dithiothreitol and a buffer.

The above-mentioned potassium salt is free of any particular limitation as long as it does not inhibit the action of the present invention, and can be used in a general form, such as potassium acetate, potassium carbonate, potassium hydrogen carbonate, potassium chloride, dipotassium hydrogen phosphate, dipotassium hydrogen citrate, potassium sulfate, potassium dihydrogen phosphate, potassium iodide, potassium phthalate and the like, with preference given to potassium acetate. Potassium salt acts as a cofactor in the protein synthesis reaction.

The content of the potassium salt in a solution for extraction is free of any particular limitation, but from the aspect of preservation stability, it is preferably 10 mM-500 mM, more preferably 50 mM-300 mM, in the case of a monovalent potassium salt, such as potassium acetate and the like. When the content of the potassium salt is less than 10 mM or more than 500 mM, the components essential for protein synthesis tend to become unstable.

The above-mentioned magnesium salt is free of any particular limitation as long as it does not inhibit the action of the present invention, and can be used in a general form such as magnesium acetate, magnesium sulfate, magnesium chloride, magnesium citrate, magnesium hydrogen phosphate, magnesium iodide, magnesium lactate, magnesium sulfate, magnesium oxalate and the like, with preference given to magnesium acetate. Magnesium salt also acts as a cofactor in the protein synthesis reaction.

The content of the magnesium salt in the extract solution is free of any particular limitation, but from the aspect of preservation stability, it is preferably 0.1 mM-10 mM, more preferably 0.5 mM-5 mM, in the case of a divalent salt, such as magnesium acetate and the like. When the content of the magnesium salt is less than 0.1 mM or more than 10 mM, the components essential for protein synthesis tend to become unstable.

The above-mentioned dithiothreitol (hereinafter sometimes to be referred to as "DTT") is added for prevention of oxidization, and is preferably contained in an amount of 0.1 mM-10 mM, more preferably 0.5 mM-5 mM, in the extract solution. When the content of DTT is less than 0.1 mM or more than 10 mM, the components essential for protein synthesis tend to become unstable.

The above-mentioned buffer imparts a buffer capacity to an extract solution, and is added for prevention of denaturation of an extract caused by a radical change in pH of the extract solution, which is due to, for example, addition of an acidic or basic substance and the like. Such buffer is free of any particular limitation, and, for example, HEPES-KOH, Tris-HCl, acetic acid-sodium acetate, citric acid-sodium citrate, phosphoric acid, boric acid, MES, PIPES and the like can be used.

The buffer is preferably one that maintains the pH of the extract solution at 4-10, more preferably pH 6.5-8.5. When the pH of the extract solution is less than 4 or more than 10, the components essential for the reaction of the present invention may be denatured. From this aspect, the use of HEPES-KOH (pH 6.5-8.5) is particularly preferable among the above-mentioned buffers.

While the content of the buffer in the extract solution is free of any particular limitation, it is preferably 5 mM-200 mM, more preferably 10 mM-100 mM, to maintain preferable buffer capacity. When the content of the buffer is less than 5 mM, pH tends to change radically due to the addition of an acidic or basic substance, which in turn may cause denaturation of the extract, and when the content of the buffer exceeds 200 mM, the salt concentration becomes too high and the components essential for protein synthesis tend to become unstable.

Furthermore, by the use of a solution for extraction further containing calcium chloride and glycerol in addition to the above-mentioned compositions, an insect cell extract solution having more improved protein synthesis ability can be preferably obtained.

In this case, the content of calcium chloride is not particularly limited. For effective exertion of the effect of the above-mentioned improved protein synthesis ability, it is preferably 0.1 mM-10 mM, more preferably 0.5 mM-5 mM. In addition, while the amount of glycerol to be added is not particularly limited, for effective exertion of the effect of the above-mentioned improved protein synthesis ability, it is preferably added in a proportion of 5 (v/v) %-80 (v/v) %, more preferably 10 (v/v) %-50 (v/v) %.

In the preparation method of the insect cell extract solution of the present invention, the steps after cell rupture to the obtainment of an insect cell extract solution for cell-free protein synthesis are not particularly limited. FIG. 1 is a simplified flowchart showing the preferable Preparation Methods 1-3 of the present invention. In each of the Preparation Methods 1-3 shown in FIG. 1, the cell is ruptured by a method comprising, after the aforementioned rapid freezing, thawing and centrifugation.

As shown in FIG. 1, after the cell rupture in the preparation method of the present invention, the supernatant (supernatant 1A) after the above-mentioned centrifugation may be used as it is as an extract solution, or supernatant 1A may be further subjected to centrifugation (10,000×g-100,000×g, 0° C.-10° C., 10 min-120 min) and the obtained supernatant (supernatant 1B) may be used as an extract solution (supernatant 1) (hereinafter to be referred to as Preparation Method 1). Moreover, the above-mentioned supernatant 1 (supernatant 1A or 1B) may be applied to gel filtration, and a fraction (fraction having high absorbance) having an absorbance at 280 nm of not less than 10 is obtained from the filtrate after gel filtration and used as an extract solution (hereinafter to be referred to as Preparation Method 2). In this case, the following steps are concretely performed.

First, the supernatant 1A or supernatant 1B is subjected to gel filtration. For the gel filtration, for example, a desalting column PD-10 (manufactured by Amersham Biosciences) can be preferably used. According to conventional methods, the column is equilibrated with a buffer solution for gel filtration, a sample is fed and eluted using the above-mentioned buffer solution for gel filtration. As the above-mentioned buffer solution for gel filtration, conventionally known buffer solutions having appropriate compositions can be used without any particular limitation. For example, a buffer solution for gel filtration containing 10 mM-100 mM HEPES-KOH (pH 6.5-8.5), 50 mM-300 mM potassium acetate, 0.5 mM-5 mM magnesium acetate, 0.5 mM-5 mM DTT and 0.01 mM-5 mM PMSF can be used. The filtrate obtained by gel filtration may be fractionated into 0.1 mL-1 mL fractions as in general gel filtration, and 0.4 mL-0.6 mL is preferably used as one fraction, for efficiently obtaining a fraction having high protein synthesis ability.

Subsequently, a fraction having an absorbance at 280 nm of not less than 30 is separated from the filtrate after gel filtration, using instruments such as Ultrospec 3300 pro (manufactured by Amersham Biosciences), to give the extract solution.

The fraction having high absorbance, which is obtained in the above-mentioned Preparation Method 2, may be further subjected to centrifugation and the obtained supernatant (supernatant 2) may be used as an extract solution (hereinafter to be referred to as Preparation Method 3). The centrifugation after gel filtration is preferably conducted at 30,000×g-100,000×g, 0° C.-10° C., 10 min-60 min, for removal of insoluble components that inhibit translation reaction.

The insect cell to be subjected to the preparation method of the present invention is preferably washed in advance, before the above-mentioned rapid freezing, with a wash solution having the same composition as the aforementioned preferable solution for extraction for insect cell, except that it does not contain a protease inhibitor and glycerol, so that the medium used for culture will not be brought into the translation reaction. Washing with a wash solution include addition of the wash solution to an insect cell, and centrifugation thereof (e.g., 700×g, 10 min, 4° C.). The amount of the wash solution to be used for the washing is preferably 5 mL-100 mL, more preferably 10 mL-50 mL, per 1 g (wet weight) of insect cell, for complete removal of the medium. The frequency of washing is preferably 1-5 times, more preferably 2-4 times.

In addition, while the amount of the insect cell to be subjected to the preparation method of the present invention is not particularly limited, it is preferably 0.1 g-5 g, more preferably 0.5 g-2 g, per 1 mL of the extract solution, to maintain optimum extraction efficiency.

The insect cell extract solution for cell-free protein synthesis, which is prepared according to the method of the present invention, preferably contains an extract derived from the insect cell in a protein concentration of 1 mg/mL-200 mg/mL, more preferably 10 mg/mL-100 mg/mL. When the content of the extract in a protein concentration is less than 1 mg/mL, the concentration of the components essential for achieving the present invention becomes lower, risking completion of sufficient synthesis reaction. When the content of the extract in a protein concentration exceeds 200 mg/mL, the extract solution itself comes to have high viscosity, making operation difficult.

The content of the extract derived from an insect cell in the extract solution is determined by measuring the protein concentration. For example, it is determined by measuring the protein concentration using a BCA Protein assay Kit (manufactured by PIERCE). To be specific, 0.1 mL of a sample is added to 2 mL of a reaction reagent, the mixture is reacted at 37° C. for 30 min and, using a spectrophotometer (Ultrospec 3300 pro, manufactured by Amersham Biosciences), the absorbance at 562 nm is measured. For control, bovine serum albumin (BSA) is generally used to form a standard curve, whereby the measurement is completed.

Whether or not the extract contained in the extract solution is derived from an insect cell is determined by, for example, base sequence analysis of ribosomal RNA in an extract solution.

The extract solution of the present invention is preferably realized to contain the extract derived from an insect cell in a protein concentration of 10 mg/mL-100 mg/mL, concurrently with 50 mM-300 mM of potassium acetate, 0.5 mM-5 mM of magnesium acetate, 0.5 mM-5 mM of DTT, 0.01 mM-5 mM of PMSF and 10 mM-100 mM of HEPES-KOH (pH 6.5-8.5).

The insect cell extract solution of the present invention is preferably subjected to a nuclease treatment before cell-free protein synthesis. By subjecting an insect cell extract solution after nuclease treatment to cell-free protein synthesis, a greater amount of an object protein can be synthesized as compared to the use of an insect cell extract solution free of a nuclease treatment. This is attributable to the following.

When the object protein is synthesized in a cell-free system, the presence of endogenous mRNA derived from a cell extract solution causes synthesis of a protein encoded by this endogenous mRNA. When an object protein is to be labeled in a cell-free system, for example, the protein synthesized by this endogenous mRNA is simultaneously labeled and may pose a problem in the subsequent object protein analysis. In addition, the amount of the synthesized object protein highly likely decreases in the presence of an endogenous mRNA. Thus, an endogenous mRNA is desirably not contained in a cell extract solution used for the cell-free protein synthesis.

While appropriate conventionally known methods can be used for the nuclease treatment without any particular limitation, since only mRNA in endogenous RNAs is selectively digested, it is preferable to treat an insect cell extract solution with Micrococcal nuclease that selectively degrades mRNA in the presence of calcium.

To be specific, Micrococcal nuclease (manufactured by Roche Diagnostics) and calcium chloride are added to an insect cell extract solution, and the mixture is reacted at 15° C.-25° C. for 5 min-60 min. Because Micrococcal nuclease may decompose, after the start of the translation reaction, exogenous mRNA or components essential for protein synthesis, which are in the extract solution, it is preferably added to the final concentration of 10 μg/mL-100 μg/mL, more preferably 30 μg/mL-60 μg/mL. Moreover, calcium chloride is preferably added to the final concentration of 0.05 mM-50 mM, more preferably 0.1 mM-1 mM, since it may inhibit the translation reaction, though calcium is essential for activation of Micrococcal nuclease. After the above-mentioned reaction, calcium ion is chelated because Micrococcal nuclease is calcium dependent, and ethylene glycol bis(2-aminoethyl ether)tetraacetic acid (hereinafter sometimes referred to as EGTA) is added to inactivate the Micrococcal nuclease. The EGTA is preferably added to the final concentration of 0.1 mM-100 mM, more preferably 1 mM-20 mM, so that the calcium ion can be sufficiently chelated.

The present invention also provides a method for cell-free protein synthesis using the above-mentioned extract solution. For such a synthesis reaction, a reaction solution generally containing the above-mentioned extract solution and additives necessary for protein synthesis in a cell-free system is prepared. The above-mentioned additive is not particularly limited and any additive can be used as long as it is conventionally used in the field of protein synthesis in a cell-free system.

The above-mentioned reaction solution is preferably prepared in such a manner that the extract solution of the present invention is contained in a proportion of 10 (v/v) %-80 (v/v) %, particularly 30 (v/v) %-60 (v/v) %.

In other words, it is preferably prepared in such a manner that the content of the extract derived from insect cells is 0.1 mg/mL-160 mg/mL, more preferably 3 mg/mL-60 mg/mL, throughout the above-mentioned reaction solution. When the content of the extract is less than 0.1 mg/mL or above 160 mg/mL in a protein concentration, the synthesis rate of the object protein may become lower.

Generally, the above-mentioned reaction solution contains, as components other than the above-mentioned extract solution, at least potassium salt, magnesium salt, DTT, adenosine 5'-triphosphate, guanosine 5'-triphosphate, creatine phosphate, creatine kinase, amino acid component, RNase inhibitor, tRNA, exogenous mRNA and buffer. This realizes a reaction solution for cell-free protein synthesis, which has an advantage in that it can synthesize a large amount of protein in a short time.

As the potassium salt in the reaction solution, various potassium salts described above as a component of solution for extraction, preferably potassium acetate, can be preferably used. The potassium salt is preferably contained in the reaction solution in a proportion of 10 mM-500 mM, more preferably 50 mM-150 mM, from the same aspect of the potassium salt in the aforementioned solution for extraction.

As a magnesium salt in the reaction solution, various magnesium salt described above as a component of solution for extraction, preferably magnesium acetate, can be preferably used. The magnesium salt is preferably contained in the reaction solution in a proportion of 0.1 mM-10 mM, more preferably 0.5 mM-3 mM, from the same aspect of the magnesium salt in the aforementioned extract solution.

DTT is preferably contained in the reaction solution in a proportion of 0.1 mM-10 mM, more preferably 0.2 mM-5 mM, from the same aspect of DTT in the aforementioned solution for extraction.

The adenosine 5'-triphosphate (hereinafter sometimes to be referred to as "ATP") is preferably contained in the reaction solution in a proportion of 0.01 mM-10 mM, more preferably 0.1 mM-5 mM, in view of the rate of protein synthesis. When ATP is contained in a proportion of less than 0.01 mM or above 10 mM, the synthesis rate of the protein tends to become lower.

The guanosine 5'-triphosphate (hereinafter sometimes to be referred to as "GTP") is preferably contained in the reaction solution in a proportion of 0.01 mM-10 mM, more preferably 0.05 mM-5 mM, in view of the rate of protein synthesis. When GTP is contained in a proportion of less than 0.01 mM or above 10 mM, the synthesis rate of the protein tends to become lower.

The creatine phosphate in the reaction solution is a component for continuous synthesis of protein and added for regeneration of ATP and GTP. The creatine phosphate is preferably contained in the reaction solution in a proportion of 1 mM-200 mM, more preferably 10 mM-100 mM, in view of the rate of protein synthesis. When creatine phosphate is contained in a proportion of less than 1 mM, sufficient amounts of ATP and GTP may not be regenerated easily. As a result, the rate of protein synthesis tends to become lower. When creatine phosphate exceeds 200 mM, it acts as an inhibitory substance and the rate of protein synthesis tends to become lower.

The creatine kinase in the reaction solution is a component for continuous synthesis of protein and added along with creatine phosphate for regeneration of ATP and GTP. The creatine kinase is preferably contained in the reaction solution in a proportion of 1 μg/mL-1000 μg/mL, more preferably 10 μg/mL-500 μg/mL, in view of the rate of protein synthesis. When the creatine kinase content is less than 1 μg/mL, sufficient amount of ATP and GTP may not be regenerated. As a result, the rate of protein synthesis tends to become lower. When the creatine kinase content exceeds 1000 μg/mL, it acts as an inhibitory substance and the synthesis rate of the protein tends to become lower.

The amino acid component in the reaction solution contains at least 20 kinds of amino acids, i.e., valine, methionine, glutamic acid, alanine, leucine, phenylalanine, glycine, proline, isoleucine, tryptophan, asparagine, serine, threonine, histidine, aspartic acid, tyrosine, lysine, glutamine, cysteine and arginine. This amino acid includes amino acid labeled with radioisotope. Where necessary, moreover, it may contain a modified amino acid. The amino acid component generally contains almost an equal amount each of the above-mentioned 20 kinds of amino acids.

In the present invention, the above-mentioned amino acid component is preferably contained in the reaction solution in a proportion of 1 μM-1000 μM, more preferably 10 μM-200 μM, in view of the rate of protein synthesis. When the amount of the amino acid component is less than 1 μM or above 1000 μM, the synthesis rate of the protein tends to become lower.

The RNase inhibitor in the reaction solution is added to prevent RNase, which is derived from insect cells contaminating the extract solution, from undesirably digesting mRNA and tRNA, thereby preventing synthesis of protein, during cell-free protein synthesis of the present invention. It is preferably contained in the reaction solution in a proportion of 0.1 U/μL-100 U/μL, more preferably 1 U/μL-10 U/μL. When the amount of RNase inhibitor is less than 0.1 U/μL, the degradation activity of RNase often cannot be suppressed sufficiently, and when the amount of the RNase inhibitor exceeds 100 U/μL, protein synthesis reaction tends to be inhibited.

As regards the exogenous mRNA in the reaction solution, a protein (including peptide) to be encoded thereby is not particularly limited as long as the mRNA is not derived from an insect cell, and the mRNA may encode a toxic protein or a glycoprotein. Whether the mRNA contained in the reaction solution is an exogenous mRNA or mRNA derived from an insect cell can be determined by isolating and purifying the mRNA from an extract solution, synthesizing cDNA using a reverse transcriptase, analyzing a base sequence of the obtained cDNA and comparing the base sequences with the base sequences of known exogenous mRNAs.

The exogenous mRNA to be used is not particularly limited as regards the number of bases and all the exogenous mRNAs may not have the same number of bases as long as they can synthesize the object protein. In addition, as long as the sequences are homologous to the degree allowing synthesis of the object protein, plural bases of each exogenous mRNA may be deleted, substituted, inserted or added.

The exogenous mRNA to be used for the present invention may be a commercially available one or an mRNA obtained by inserting ORF (Open reading frame) of the object protein into the downstream of the 5'-β-globin leader sequence of a commercially available vector, such as pTNT Vector (manufactured by Promega), and performing a transcription reaction using the resulting vector. Furthermore, an exogenous mRNA having a cap structure resulting from the addition of methylated ribonucleotide and the like during transcription reaction may be used.

An exogenous mRNA is preferably contained in the reaction solution in a proportion of 5 µg/mL-2000 µg/mL, more preferably 20 µg/mL-1000 µg/mL, in view of the protein synthesis rate. When the amount of exogenous mRNA is less than 5 µg/mL or exceeds 2000 µg/mL, the rate of protein synthesis tends to decrease.

The tRNA in the reaction solution contains almost an equal amount each of the tRNAs corresponding to the above-mentioned 20 kinds of amino acids. In the present invention, tRNA is preferably contained in the reaction solution in a proportion of 1 µg/mL-1000 µg/mL, more preferably 10 µg/mL-500 µg/mL, in view of the rate of protein synthesis. When the amount of tRNA is less than 1 µg/mL or exceeds 1000 µg/mL, the rate of protein synthesis tends to become lower.

The buffer to be contained in the reaction solution is preferably similar to those used for the aforementioned extract solution of the present invention, and the use of HEPES-KOH (pH 6.5-8.5) is preferable for the same reasons. The buffer is preferably contained in the amount of 5 mM-200 mM, more preferably 10 mM-50 mM, from the same aspect as in the aforementioned buffer contained in the extract solution.

The above-mentioned reaction solution preferably contains EGTA. This is because EGTA in an extract solution forms a chelate with a metal ion therein and inactivates ribonuclease, protease and the like, thereby inhibiting decomposition of the components essential for protein synthesis in the present invention. Even when a nuclease treatment is applied to an extract solution as mentioned above, an adverse influence of nuclease on the cell-free protein synthesis can be certainly prevented because the reaction solution contains EGTA. EGTA is preferably contained in the above-mentioned reaction solution at 0.01 mM-50 mM, more preferably 0.1 mM-10 mM, in view of preferable exertion of the above-mentioned decomposition inhibitory ability. When EGTA is contained in less than 0.01 mM, decomposition of essential components cannot be sufficiently suppressed. When it exceeds 50 mM, it tends to inhibit protein synthesis reaction.

In other words, the reaction solution to be used for the cell-free protein synthesis method of the present invention is preferably made to contain the above-mentioned extract solution in a proportion of 30 (v/v) %-60 (v/v) %, together with 50 mM-150 mM of potassium acetate, 0.5 mM-3 mM of magnesium acetate, 0.2 mM-5 mM of DTT, 0.1 mM-5 mM of ATP, 0.05 mM-5 mM of GTP, 10 mM-100 mM of creatine phosphate, 10 µg/mL-500 µg/mL of creatine kinase, 10 µM-200 µM of amino acid component, 1 U/µL-10 U/µL of RNase inhibitor, 10 µg/mL-500 µg/mL of tRNA, 20 µg/mL-1000 µg/mL of exogenous mRNA and 10 mM-50 mM of HEPES-KOH (pH 6.5-8.5). In addition, the reaction solution is more preferably made to contain 0.1 mM-10 mM of EGTA in addition to the above.

The cell-free protein synthesis method of the present invention is performed using the extract solution of the present invention mentioned above, in, for example, a conventionally known low temperature incubator. For the reaction, a reaction solution containing the above-mentioned extract solution is generally prepared and used.

The reaction temperature is generally within the range of 10° C.-40° C., preferably 15° C.-30° C. When the reaction temperature is lower than 10° C., the synthesis rate of the protein tends to become lower, and when the reaction temperature exceeds 40° C., the essential components tend to be denatured.

The reaction time is generally 1 hr-72 hr, preferably 3 hr-24 hr.

The present invention relates to a kit for cell-free protein synthesis, which contains an insect cell extract solution of the present invention. It is preferable that the insect cell extract solution contained in the kit has been treated with nuclease. It is more preferable that the insect cell be a culture cell derived from *Trichoplusia ni* ovum or *Spodoptera frugiperda* ovary cell.

Preferably, the kit further contains all or a part of the group consisting of a potassium salt, a magnesium salt, DTT, adenosine 5'-triphosphate, guanosine 5'-triphosphate, creatine phosphate, creatine kinase, an amino acid component, an RNase inhibitor, tRNA and a buffer. These components are contained in the kit in the form of a powder or a solution. All or a part of these components may be contained in a mixed state in the kit. The constituent components of the kit are preferably packaged separately and contained in one package.

The amount of protein synthesized by the cell-free protein synthesis method of the present invention can be measured by activity assay of enzyme, SDS-PAGE, immunoassay and the like.

The protein synthesized by the cell-free protein synthesis method of the present invention is free of any particular limitation.

EXAMPLES

The present invention is explained in detail in the following by way of Examples, which are not to be construed as limitative.

Reference Example 1

Culture of Insect Cells

High Five (manufactured by Invitrogen) insect cells (2.1×$10^7$ cells) were cultured in a culture flask (600 cm$^2$) containing an Express Five serum-free medium (manufactured by Invitrogen) supplemented with L-glutamine at 27° C. for 6 days. As a result, the cell count reached $1.0 \times 10^8$ and wet weight 1.21 g.

Example 1

Preparation of Insect Cell Extract Solution

The insect cells cultured in the above-mentioned Reference Example 1 were collected, washed (centrifugation at 700×g, 4° C., 10 min) 3 times with a solution for extraction having the following composition and then suspended in 1 mL of a solution for extraction.

| [Composition of solution for extraction] | |
|---|---|
| 60 mM | HEPES-KOH (pH 7.9) |
| 200 mM | potassium acetate |
| 4 mM | magnesium acetate |
| 4 mM | DTT |
| 0.5 mM | PMSF |

This suspension was rapidly (within 10 sec) frozen in liquid nitrogen. After freezing sufficiently, the suspension was thawed in a water bath at about 10° C. After complete thawing, it was subjected to centrifugation at 15000×g, 4° C. for 15 min (himacCR20B3, manufactured by Hitachi Koki) and the supernatant was recovered. The recovered supernatant (1.5 mL) was applied to PD-10 desalting column (manufactured Amersham Biosciences) equilibrated with a buffer solution for gel filtration having the following composition.

| [Composition of buffer solution for gel filtration] | |
|---|---|
| 40 mM | HEPES-KOH (pH 7.9) |
| 100 mM | potassium acetate |
| 2 mM | magnesium acetate |
| 1 mM | DTT |
| 0.5 mM | PMSF |

After the application, the supernatant was eluted with a buffer solution for gel filtration (4 mL) and fractions having absorbance at 280 nm of not less than 30 were recovered using a spectrophotometer (Ultrospec 3300 pro, manufactured by Amersham Biosciences). The recovered filtrate was further subjected to centrifugation at 45,000×g, 4° C. for 30 min and the supernatant was used as an insect cell extract solution.

Reference Example 2

Preparation of Exogenous mRNA (1) Construction of Vector DNA

Using pGEM-luc vector (5 ng, manufactured by Promega) as a template, a primer (Luc T7-F3-Kpn) having a base sequence depicted in SEQ ID; No 1, a primer (Luc T7-R4-Kpn) having a base sequence depicted in SEQ ID; No 2, and KOD plus (manufactured by TOYOBO Co.), PCR was performed at 97° C., 15 sec, 55° C., 30 sec and 68° C., 120 sec, for 30 cycles. DNA fragment was purified by ethanol precipitation, and digested with KpnI.

Separately, $pT_NT$ Vector (manufactured by Promega) was digested with KpnI. These reaction solutions were separated by agarose gel electrophoresis, and using a Gen Elute Gel Purification Kit (manufactured by SIGMA), DNA fragment was purified. Using Ligation High (manufactured by TOYOBO Co.), these DNA fragments were ligated and *Escherichia coli* DH5α (manufactured by TOYOBO Co.) was transformed. Plasmid DNA was prepared from the transformed *Escherichia coli* by alkali-SDS methods, and subjected to a sequencing reaction (96° C. 10 sec, 50° C. 5 sec, 60° C. 4 min, 30 cycles) using primer (T7 promoter) having a base sequence depicted in SEQ ID; No 3 and Big Dye Terminator Cycle Sequencing FS (manufactured by Applied Biosystems). This reaction solution was applied to ABI PRISM 310 Genetic Analyzer (manufactured by Applied Biosystems), and the base sequence was analyzed. A plasmid having a start codon of luciferase gene inserted into the downstream of $pT_NT$ Vector-derived 5'-β-globin leader sequence was named as $pT_NT$-Luc.

(2) In Vitro Transcription Reaction $pT_NT$-Luc prepared in the above-mentioned (1) was digested with BamHI, and purified by phenol-chloroform extraction and ethanol precipitation. Using this as a template, in vitro transcription reaction was carried out. The transcription reaction solution used had the following composition.

| [Composition of transcription reaction solution] | |
|---|---|
| 80 mM | HEPES-KOR (pH 7.4) |
| 24 mM | magnesium acetate |
| 40 mM | DTT |
| 7.5 mM | NTPs (ATP, GTP, UTP, CTP) |
| 2 mM | spemidine |
| 1 U/μL | RNase inhibitor (derived from human placenta) |
| 1 U/μL | T7 RNA polymerase |
| 50 μg/mL | pTNT-Luc/BamHI |

NTPs (manufactured by SIGMA), RNase inhibitor (manufactured by TAKARA SHUZO Co.) and T7 RNA polymerase (manufactured by Promega) were respectively used. As a reaction device, low temperature dry block MG-1000 (manufactured by TOKYO RIKAKIKAI Co.) was used. The transcription reaction was carried out at 37° C. for 4 hr, and the amount of the reaction solution was 20 μL.

(3) Purification of Exogenous mRNA

After the completion of the transcription reaction, 1 U RQ1 RNase free DNase (manufactured by Promega) was added to the reaction solution (20 μL) of the above-mentioned (2). The mixture was incubated at 37° C. for 15 min and the template DNA was digested. Protein was removed by phenol-chloroform extraction, and potassium acetate was added to the final concentration of 0.3 M to perform ethanol precipitation. The obtained precipitate was dissolved in 100 μL of distilled water and applied to Nick Column (manufactured by Amersham Biosciences) and eluted with distilled water (400 μL). The eluted fraction was recovered, potassium acetate was added to the final concentration of 0.3 M, and ethanol precipitation was conducted. For quantification of the synthesized exogenous mRNA, absorbance at 260 nm was measured. As a result, about 60 μg of exogenous mRNA was synthesized by 20 μL scale reaction.

Experimental Example 1

Cell-Free Protein Synthesis Using Insect Cell Extract Solution of Example 1 and Exogenous mRNA of Reference Example 2

Using the insect cell extract solution prepared in Example 1 and exogenous mRNA synthesized in Reference Example 2, a reaction solution having the following composition was prepared and protein synthesis in a cell-free system was performed.

| [Composition of reaction solution] | |
|---|---|
| 50 (v/v)% | insect cell extract solution |
| 40 mM | HEPES-KOH (pH 7.9) |
| 100 mM | potassium acetate |
| 2 mM | magnesium acetate |
| 2 mM | DTT |
| 0.5 mM | ATP |
| 0.25 mM | GTP |
| 20 mM | creatine phosphate |
| 200 µg/mL | creatine kinase |
| 80 µM | amino acid (20 kinds) |
| 0.25 mM | EGTA |
| 1 U/µL | RNase inhibitor (derived from human placenta) |
| 200 µg/mL | tRNA |
| 320 µg/mL | exogenous mRNA |

ATP (manufactured by SIGMA), GTP (manufactured by SIGMA), amino acid (20 kinds, manufactured by SIGMA), RNase inhibitor (manufactured by TAKARA SHUZO Co.), and tRNA (manufactured by Roche Diagnostics) were respectively used. As a reaction device, low temperature dry block MG-1000 was used. The amount of the reaction solution was 25 µL, the reaction temperature was 25° C., a sample was taken for each reaction time and the amount of synthesized luciferase was measured. The synthesized luciferase was quantified using a luciferase assay kit (E-1500, manufactured by Promega). The reaction solution (2.5 µL) was added to a luciferase assay reagent (50 µL) and luminescence by luciferase was measured using a luminometer (Tuner Designs TD-20/20, manufactured by Promega).

Figure 2:
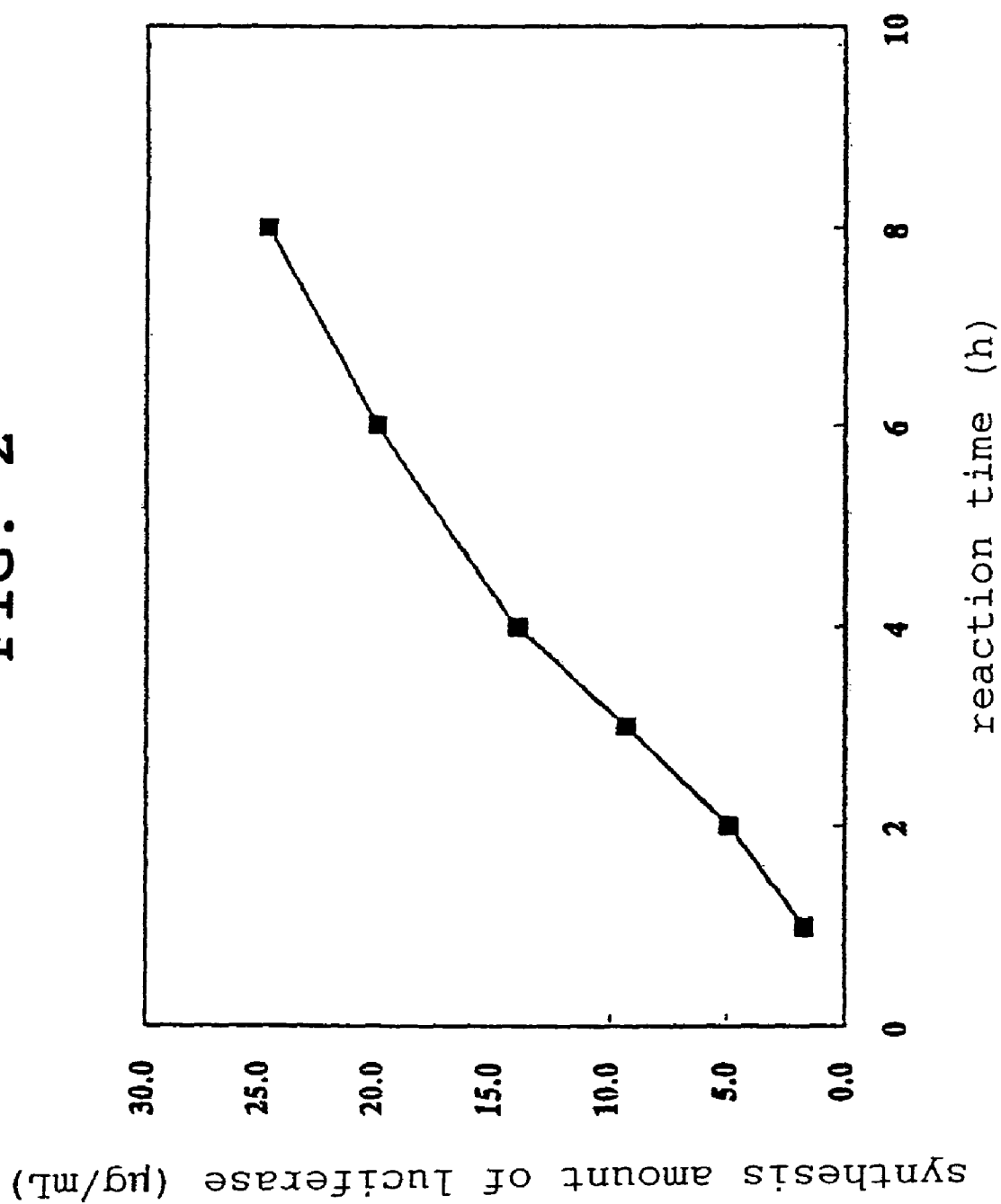
FIG. 2 is a graph showing an amount of synthesized luciferase in each reaction time using the insect cell extract solution of Example 1, wherein the axis of ordinate shows the amount of synthesized luciferase (μg/mL) and the axis of abscissa shows the reaction time (h).

FIG. 2 is a graph showing an amount of synthesized luciferase at each reaction time using the insect cell extract solution of Example 1. In FIG. 2, the axis of ordinate shows the amount of synthesized luciferase (µg/mL) and the axis of abscissa shows the reaction time (h). As shown in FIG. 2, the protein synthesis reaction continued for 8 hr after the start of the reaction and 24.7 µg/mL of luciferase was synthesized.

Example 2

Nuclease Treatment of Insect Cell Extract Solution of Example 1

To the extract solution of Example 1 were added Micrococcal nuclease (manufactured by Roche Diagnostics, final concentration 36 µg/mL) and calcium chloride (final concentration 0.36 mM), and the mixture was reacted at 20° C. for 15 min. After the reaction, EGTA was added to the final concentration of 6 mM and the mixture was used as an insect cell extract solution.

Experimental Example 2

Cell-Free Protein Synthesis Using Insect Cell Extract Solution of Example 2 and Exogenous mRNA of Reference Example 2

In the same manner as in Experimental Example 1 except that the insect cell extract solution prepared in Example 2 and exogenous mRNA synthesized in Reference Example 2 were used, a reaction solution having a similar composition as in Example 1 was prepared and subjected to protein synthesis in a cell-free system.

Figure 3:
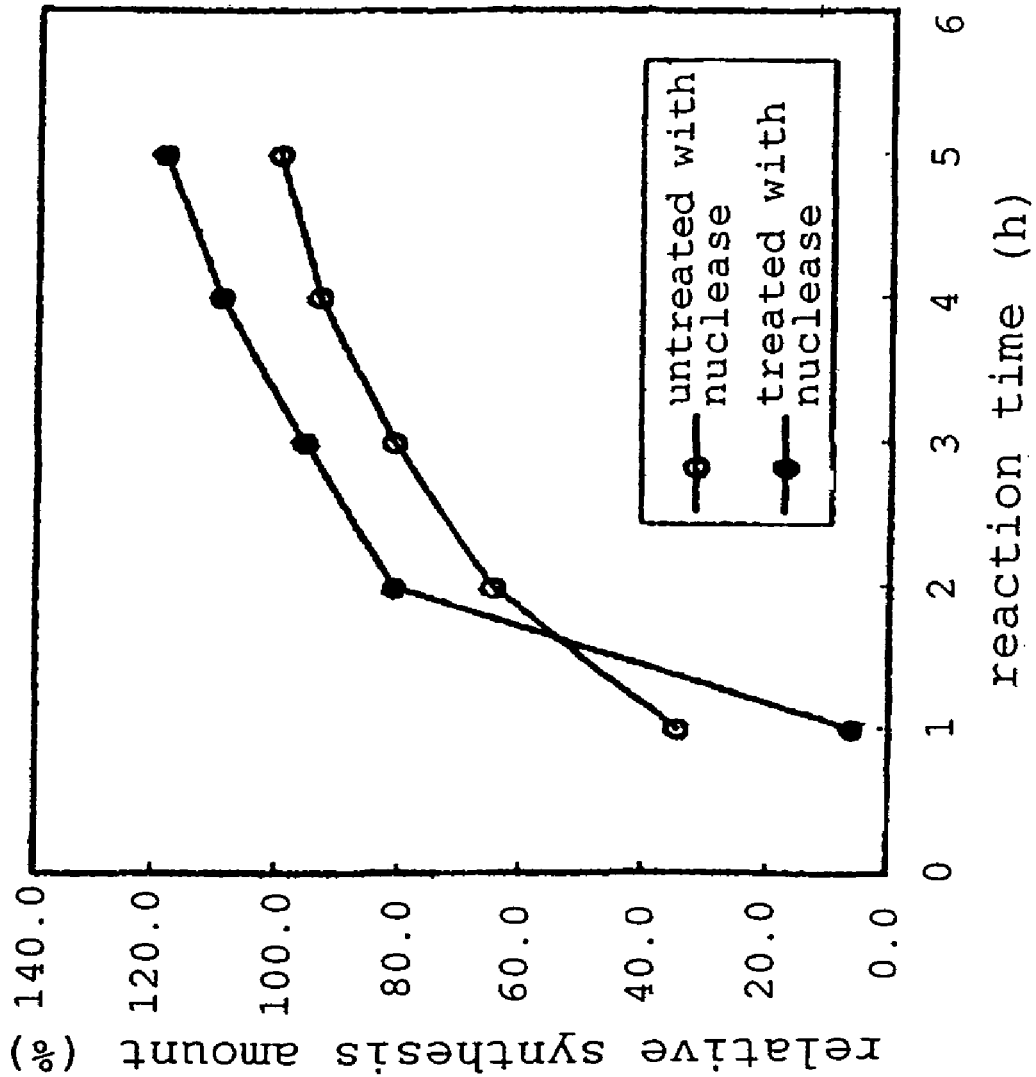
FIG. 3 is a graph showing changes in the amount of synthesized luciferase in 5 hr from the start of the synthesis reaction using the insect cell extract solutions of Experimental Examples 1 and 2, wherein the axis of ordinate shows a synthesis amount (%) relative to luciferase content of the reaction solution using a nuclease untreated extract solution 5 hr later as 100%, and the axis of abscissa shows the reaction time (h).

FIG. 3 is a graph showing changes in the amount of synthesized luciferase in 5 hr from the start of the synthesis reaction using the insect cell extract solution of Experimental Examples 1 and 2. In FIG. 3, the axis of ordinate shows a synthesis amount (%) relative to the luciferase content of the reaction solution using a nuclease untreated extract solution 5 hr later as 100%, and the axis of abscissa shows the reaction time (h). As shown in FIG. 3, it has been clarified that the synthesis amount of protein increases when the nuclease treated insect cell extract solution of Example 2 is used.

Reference Example 3

Addition of Cap Structure

The 7-methylguanosine 5' cap structure seen in many eukaryote-derived mRNAs is known to stabilize mRNA and improve affinity for ribosome. When methylated ribonucleotide is added during a transcription reaction, a cap structure can be incorporated into the 5' end of the transcription product. Specifically, an exogenous mRNA having a cap structure was synthesized by the following steps.

$pT_N$T-Luc produced in the same manner as in Reference Example 2(1) was digested with BamHI and purified by phenol-chloroform extraction and ethanol precipitation. Using this as a template and Ribo $m^7$ Cap Analog (manufactured by Promega) as methylated ribonucleotide, in vitro transcription reaction was conducted. The composition of the transcription reaction solution is shown in the following.

| [Composition of transcription reaction solution] | |
|---|---|
| 80 mM | HEPES-KOH (pH 7.9) |
| 24 mM | magnesium acetate |
| 40 mM | DTT |
| 7.5 mM | ATP |
| 7.5 mM | UTP |
| 7.5 mM | CTP |
| 0.6 mM | GTP |
| 3 mM | Ribo $m^7$ Cap Analog |
| 2 mM | spermidine |
| 1 U/µL | RNase inhibitor (derived from human placenta) |
| 1 U/µL | T7 RNA polymerase |
| 50 µg/mL | $pT_N$T-Luc/BamHI |

Experimental Example 3

A reaction solution having the same composition as in Experimental Example 1 was prepared except that the insect cell extract solution prepared in Example 1 and exogenous mRNA having a cap structure synthesized in Reference Example 3 were used, and protein was synthesized in a cell-free system. As a result, about 2.6 times the amount of luciferase produced by an exogenous mRNA free of a cap structure (Experimental Example 1) was synthesized in a reaction time of 10 hr.

Figure 4:
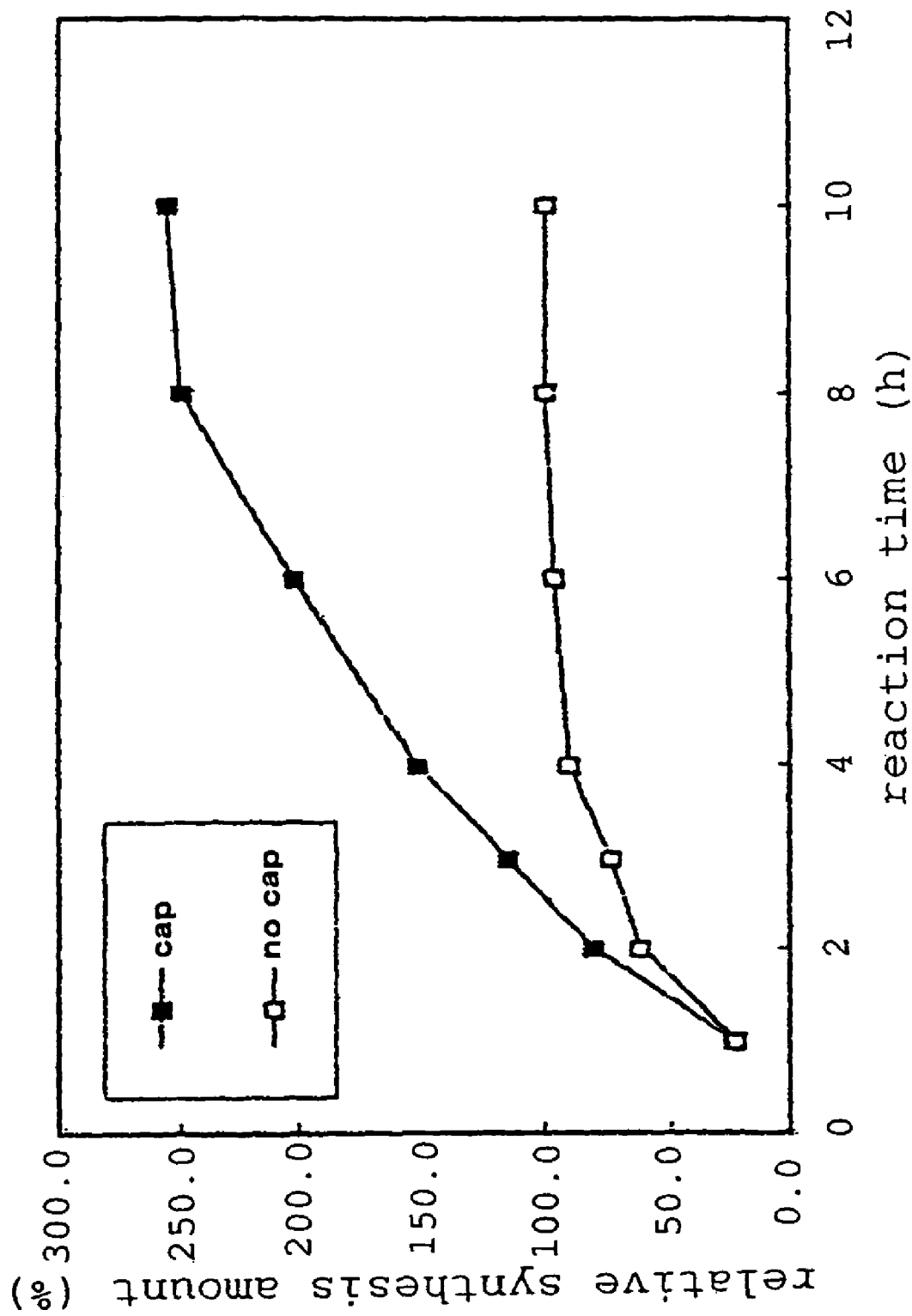
FIG. 4 is a graph showing changes in the amount of synthesized luciferase in 10 hr from the start of the synthesis reaction using the insect cell extract solution of Example 1 and the mRNA of Reference Example 3.

FIG. 4 is a graph showing changes in the amount of synthesized luciferase in 10 hr from the start of the synthesis reaction using the insect cell extract solution of Example 1 and the mRNA of Reference Example 3. In FIG. 4, the axis of ordinate shows a synthesis amount (%) relative to the luciferase content of the reaction solution using the insect cell extract solution of Example 1 and an exogenous mRNA free of a cap structure (Reference Example 2) 10 hr later as 100%, and the axis of abscissa shows the reaction time (h).

Comparative Example 1

In the same manner as in Example 1 and Experimental Example 1 except that High Five (manufactured by Invitrogen) insect cells cultured in the same manner as in Reference Example 1 were cooled, suspended and vigorously stirred for 5 min for extraction, protein synthesis was conducted in a cell-free system.

As a result, the reaction stopped in 2 hr, and the amount of synthesized luciferase was 20 ng/mL, which was about 1/1000 of Experimental Example 1.

Comparative Example 2

In the same manner as in Example 1 and Experimental Example 1 except that High Five (manufactured by Invitrogen) insect cells cultured in the same manner as in Reference Example 1 were dissolved in a reagent for cell lysis (Cell Culture Lysis Reagent, manufactured by Promega) and then extracted, protein synthesis was conducted in a cell-free system.

As a result, the reaction stopped in 2 hr, and the amount of synthesized luciferase was 200 ng/mL, which was about 1/100 of Experimental Example 1.

Reference Example 4

Culture of Insect Cell

Sf21 (manufactured by Invitrogen) insect cells were cultured in an Sf900-II serum-free medium (manufactured by Invitrogen) at 27° C. $6.0 \times 10^5$ cells of Sf21 per 1 mL medium were cultured in a suspension state in a medium (50 mL) in a 125 mL Erlenmeyer flask at 27° C., 130 rpm for 5 days. As a result, the cell count per 1 mL of medium reached $1.0 \times 10^8$ and wet weight 3 g. Using the cells, a cell extract solution was prepared.

Example 3

Preparation of Insect Cell Extract Solution

First, the insect cells cultured in the above-mentioned Reference Example 4 were collected, washed (centrifugation 700×g, 4° C., 10 min) 3 times with a wash solution having the following composition, and suspended in 3 mL of a solution for extraction having the following composition.

| [composition of wash solution] | |
|---|---|
| 40 mM | HEPES-KOH (pH 7.9) |
| 100 mM | potassium acetate |
| 2 mM | magnesium acetate |
| 2 mM | calcium chloride |
| 1 mM | DTT |

| [composition of solution for extraction] | |
|---|---|
| 40 mM | HEPES-KOH (pH 7.9) |
| 100 mM | potassium acetate |
| 2 mM | magnesium acetate |
| 2 mM | calcium chloride |
| 20% (v/v) | glycerol |
| 1 mM | DTT |
| 0.5 mM | PMSF |

This cell suspension was rapidly (within 10 sec) frozen in liquid nitrogen. After freezing sufficiently, the suspension was thawed in an ice-water bath at about 4° C. After complete thawing, it was subjected to centrifugation at 30,000×g, 4° C. for 10 min (himacCR20B3, manufactured by Hitachi Koki) and supernatant 1A was recovered. The recovered supernatant 1A was further subjected to centrifugation (himacCR20B3, manufactured by Hitachi Koki) at 45000×g, 4° C. for 30 min to give supernatant 1B. The recovered supernatant 1B (2.5 mL) was applied to PD-10 desalting column (manufactured Amersham Biosciences) equilibrated with a buffer solution for gel filtration having the following composition.

| [Composition of a buffer solution for gel filtration] | |
|---|---|
| 40 mM | HEPES-KOH (pH 7.9) |
| 100 mM | potassium acetate |
| 2 mM | magnesium acetate |
| 1 mM | DTT |
| 0.5 mM | PMSF |

After the application, the supernatant was eluted with a buffer solution for gel filtration (3 mL) and fractions having absorbance at 280 nm of not less than 30 were recovered using a spectrophotometer (Ultrospec 3300 pro, manufactured by Amersham Biosciences) and used as an insect cell extract solution.

Experimental Example 4

Cell-Free Protein Synthesis Using Insect Cell Extract Solution of Example 3 and Exogenous mRNA of Reference Example 2

Using the insect cell extract solution prepared in Example 3 and exogenous mRNA synthesized in Reference Example 2, a reaction solution having the following composition was prepared and subjected to protein synthesis in a cell-free system.

| [Composition of reaction solution] | |
|---|---|
| 50 (v/v)% | insect cell extract solution |
| 40 mM | HEPES-KOH (pH 7.9) |
| 100 mM | potassium acetate |
| 1.5 mM | magnesium acetate |
| 2 mM | DTT |
| 0.25 mM | ATP |
| 0.1 mM | GTP |
| 20 mM | creatine phosphate |
| 200 μg/mL | creatine kinase |
| 80 μM | amino acid (20 kinds) |
| 0.1 mM | EGTA |

-continued

| [Composition of reaction solution] | |
|---|---|
| 1 U/μL | RNase inhibitor |
| 200 μg/mL | tRNA |
| 320 μg/mL | exogenous mRNA(coding a luciferase gene) |

Figure 5:
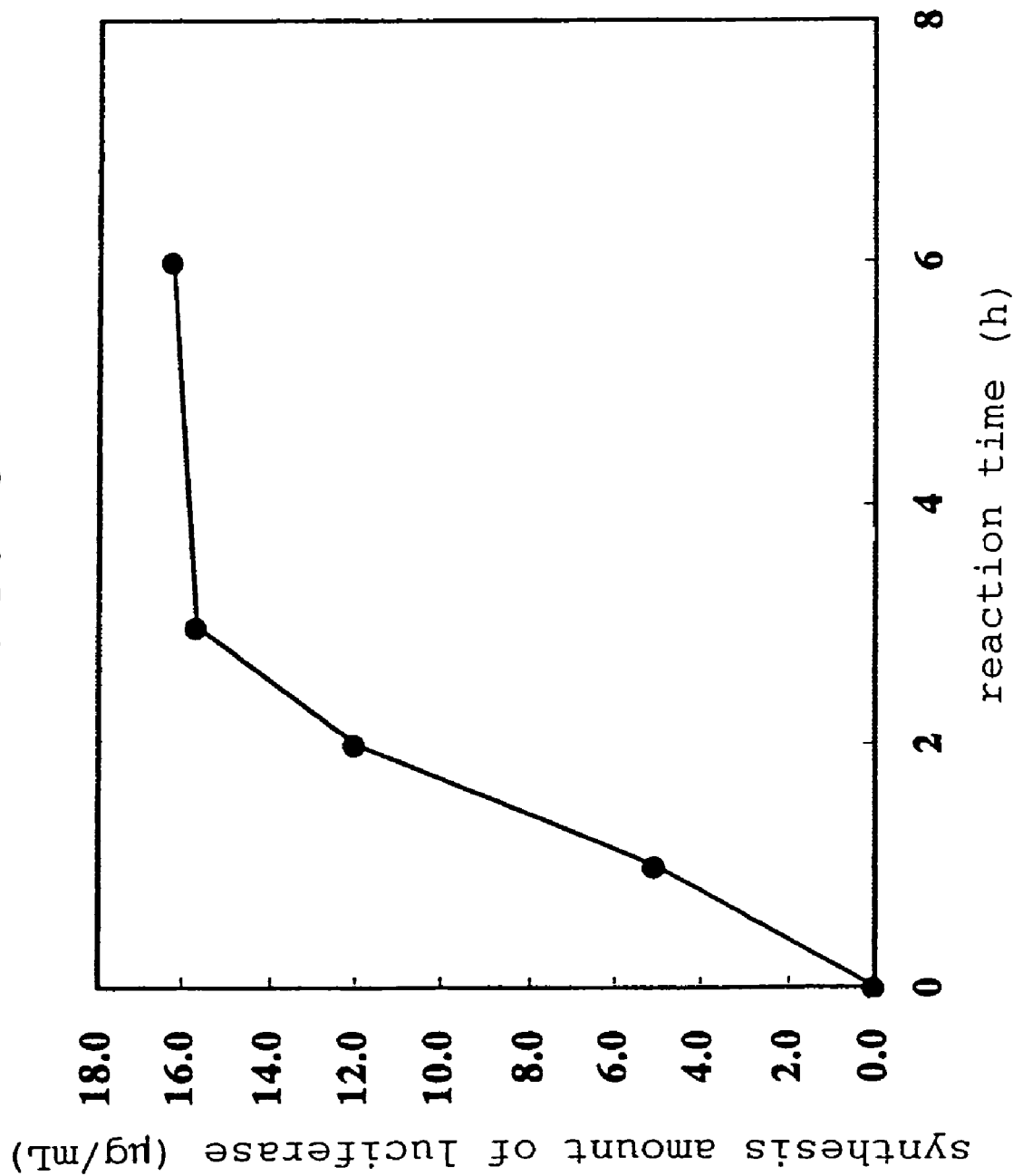
FIG. 5 is a graph showing an amount of synthesized luciferase in each reaction time using the insect cell extract solution of Example 3, wherein the axis of ordinate shows the amount of synthesized luciferase (μg/mL) and the axis of abscissa shows the reaction time (h).

ATP (manufactured by SIGMA), GTP (manufactured by SIGMA), amino acid (20 kinds, manufactured by SIGMA), RNase inhibitor (manufactured by TAKARA SHUZO Co.) and tRNA (manufactured by Roche Diagnostics) were used. As a reaction device, low temperature dry block MG-1000 was used. The amount of the reaction solution was 25 μL, reaction temperature was 25° C. and reaction time was 6 hr. In the same manner as in Experimental Example 1, the amount of synthesized luciferase was measured with time. As a result, 16.3 μg/mL of luciferase was synthesized (FIG. 5).

INDUSTRIAL APPLICABILITY

According to the present invention, a preparation method of an insect cell extract solution for cell-free protein synthesis, which solution is easy to prepare and affords synthesis of a large amount of a protein, the insect cell extract solution, a protein synthesis method in a cell-free system, which uses the insect cell extract solution, and a kit for cell-free protein synthesis, containing the insect cell extract solution are provided.

This application is based on patent application No. 382415/2002 filed in Japan, the contents of which are incorporated hereinto by reference.

Free Text of Sequence Listing

SEQ ID; No 1

Primer Luc T7-F3-Kpn

SEQ ID; No 2

Primer Luc T7-R4-Kpn

SEQ ID; No 3

Primer T7 promoter

What is claimed is:

1. A method for cell-free protein synthesis, which comprises performing cell-free protein synthesis with an insect cell extract solution, wherein the insect cell extract solution is prepared by a process which comprises at least a step of rapid freezing at a temperature not higher than −80° C. an insect cell suspended in a solution for extraction, to allow for extraction from the insect cell, wherein the rapid freezing results in the insect cell being frozen for not longer than 10 seconds; wherein the cell-free protein synthesis is performed with an exogenous mRNA having a cap structure.

2. The method of claim 1, wherein the process for preparing the insect cell extract solution further comprises thawing said insect cell after the rapid freezing and subjecting the cell to centrifugation.

3. The method of claim 2, wherein the insect cell is thawed in a water bath or ice-water bath at −10° C. to 20° C.

4. The method of claim 1, wherein the rapid freezing involves freezing the insect cell with liquid nitrogen.

5. The method of claim 1, wherein the solution for extraction for the process for preparing the insect cell extract solution comprises a protease inhibitor.

6. The method of claim 1, wherein the insect cell is a culture cell derived from *Trichoplusia ni* ovum or *Spodoptera frugiperda* ovary cell, or a combination of a cell derived from *Trichoplusia ni* ovum and a cell derived from *Spodoptera frugiperda* ovary cell.

7. The method of claim 1, wherein the rapid freezing of the insect cell is at a temperature not higher than −150° C.

8. The method of claim 1, wherein the process for preparing the insect cell extract solution further comprises subjecting the insect cell extract solution to a nuclease treatment before cell-free protein synthesis.

9. The method of claim 1, wherein the cell-free protein synthesis is performed with a reaction solution comprising the insect cell extract solution and at least one of the following: potassium salt, magnesium salt, DTT, adenosine 5'-triphosphate, guanosine 5'-triphosphate, creatine phosphate, creatine kinase, an amino acid component, RNase inhibitor, tRNA, exogenous mRNA and a buffer.

10. The method of claim 9, wherein the exogenous mRNA is an exogenous mRNA having a cap structure.

* * * * *

```
                        SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Luc T7-F3-Kpn

<400> SEQUENCE: 1
ggggtaccat ggaagacgcc aaaaacataa                                       30

<210> SEQ ID NO 2
<211> LENGTH: 29
<212> TYPE: DNA
<213> ORGANISM: Artificial Sequence
<220> FEATURE:
<223> OTHER INFORMATION: Luc T7-R4-Kpn

<400> SEQUENCE: 2
ggggtacctt acaatttgga ctttccgcc                                        29

<210> SEQ ID NO 3
<211> LENGTH: 20
<212> TYPE: DNA
<213> ORGANISM: Artificial Sequence
<220> FEATURE:
<223> OTHER INFORMATION: T7 promoter

<400> SEQUENCE: 3
taatacgact cactataggc                                                  20
```